United States Patent [19]
Cast et al.

[11] Patent Number: 6,074,881
[45] Date of Patent: Jun. 13, 2000

[54] METHOD FOR THE PREVENTION OF HEMOGLOBIN INTERFERENCE IN REAGENT SYSTEMS FOR MEASURING PEROXIDASE ACTIVITY

[75] Inventors: Todd K. Cast; Michael J. Pugia, both of Granger, Ind.

[73] Assignee: Bayer Corporation, Elkhart, Ind.

[21] Appl. No.: 09/128,009

[22] Filed: Aug. 3, 1998

[51] Int. Cl.[7] .................. G01N 33/48; G01N 33/493; G01N 33/70; C12Q 1/28
[52] U.S. Cl. ................. 436/74; 436/63; 436/66; 436/91; 436/98; 436/135; 436/166; 436/169; 436/175; 422/56; 435/4; 435/28
[58] Field of Search ................. 436/135, 63, 66, 436/71, 91–99, 127, 128, 131, 164, 166, 169, 175, 810, 904, 74; 422/56–57; 435/4, 10, 11, 14, 28

[56] References Cited

U.S. PATENT DOCUMENTS

| | | | |
|---|---|---|---|
| 4,350,762 | 9/1982 | De Luca et al. | 435/10 |
| 4,637,978 | 1/1987 | Dappen | 435/11 |
| 5,183,741 | 2/1993 | Arai et al. | 435/14 |
| 5,374,561 | 12/1994 | Pugia | 436/98 |
| 5,418,142 | 5/1995 | Kiser et al. | 435/14 |
| 5,702,955 | 12/1997 | Pugia | 436/135 |

*Primary Examiner*—Arlen Soderquist
*Attorney, Agent, or Firm*—Jerome L. Jeffers

[57] ABSTRACT

The present invention involves an improvement to an assay for the activity of a metal chelate, such as copper II/creatinine, which activity is related to the concentration of the analyte in a fluid test sample. In carrying out the assay, there is combined the fluid test sample, the metal chelate or precursors thereof, a hydroperoxide, an oxidizable indicator and a pyrazole derivative which inhibits the ability of hemoglobin to oxidize the oxidizable dye.

11 Claims, No Drawings

METHOD FOR THE PREVENTION OF HEMOGLOBIN INTERFERENCE IN REAGENT SYSTEMS FOR MEASURING PEROXIDASE ACTIVITY

BACKGROUND OF THE INVENTION

The present invention is an improvement to those methods for the detection of peroxidase activity in samples of body fluid whose sensitivity is impaired by hemoglobin interference. For example, there is disclosed in U.S. Pat. No. 5,374,561 a method for the detection of creatinine in urine which comprises contacting a urine sample suspected of containing creatinine with cupric ions, a hydroperoxide and an oxidizable dye which provides a colored response in the presence of oxygen free radicals and a hydroperoxide. In this assay, the first step involves the formation of a $Cu^{++}$•creatinine chelated complex. The oxidizable dye is oxidized by the transfer of an electron therefrom to the $Cu^{++}$•creatinine complex to provide the non-reactive $Cu^{+}$•creatinine form which is regenerated to $Cu^{++}$•creatinine by the loss of an electron to the hydroperoxide. This assay works well in the absence of hemoglobin, but in the presence of hemoglobin its precision is affected due to the tendency of hemoglobin to oxidize the dye thereby causing false positives. Since hemoglobin is frequently found in body fluids such as urine, there is a need to block its interference to thereby provide a more precise assay.

In co-pending application U.S. Ser. No. 08/990,389; there is disclosed an assay for an analyte in a fluid test sample which involves combining the fluid test sample with a reagent system comprising an apo-peroxidase, a redox dye, a hydroperoxide and a transition metal porpyhrin chelate which is bound to an analyte/analyte specific binding partner having a combined molecular weight of at least about 180 K Daltons. When this conjugate interacts with analyte in the fluid test sample, a portion of the specific binding partner is dissociated from the conjugate thereby enabling the metal porpyhrin to reconstitute with the apo-peroxidase which reconstituted peroxidase can interact with the hydroperoxide and redox dye to provide a colored response to analyte in the fluid test sample. This type of assay is also adversely affected by the presence of hemoglobin in the fluid test sample because of oxidation of the redox dye in the presence of a hydroperoxide.

Other assays involving the use of metal chelates include ferric ion/creatinine; transition metal/2,2'-dipyridyls; transition metal/diethylene polyamino polyacetic acids such as EGTA, HEDTA and NTA; transition metal/oximes; transition metal/phenianthrolines; transition metal/throcarbamides; transition metal/triethylene tetramine and transition metal catechol. The use of iron chelates, iron creatine in particular, to detect hydrogen peroxide is disclosed in U.S. Pat. No. 5,702,955.

SUMMARY OF THE INVENTION

The present invention involves an improvement to an assay for the activity of a metal chelate, which activity is related to the concentration of an analyte in a fluid test sample. The assay involves combining the fluid test sample suspected of containing the analyte with a metal chelate or precursors thereof, a hydroperoxide and a redox indicator which is oxidizable in the presence of the metal chelate and hydroperoxide to provide a colored response which is indicative of the presence of the metal chelate. The improvement involves combining the assay components with a pyrazole derivative which inhibits the ability of hemoglobin to oxidize the redox dye without substantially inhibiting the ability of the metal chelate to cause such oxidation.

DESCRIPTION OF THE INVENTION

A novel method for the colorimetric determination of creatinine concentration in fluid test samples is disclosed in U.S. Pat. No. 5,374,561. This method takes advantage of the peroxidase activity of creatinine/transition metal complexes. In this assay, the chelation of transition metals by creatinine produces a complex capable of catalyzing the oxidization of an oxidizable dye such as tetramethyl benzidine by a hydroperoxide such as diisopropyl benzene dihydroperoxide to thereby provide a colored response. It has been discovered more recently that this assay is rendered somewhat inaccurate by the reaction of hemoglobin commonly found in body fluids. This problem is resolved by the present invention which involves the discovery of a group of pyrazole derivatives which prevent hemoglobin interference in this assay. J. Ziegenhorn et al report that a pyrazole derivative, aminopyrine, is a redox indicator of peroxidase activity, especially in the presence of phenol and peroxide, in J. Clin. Chem. Clin. Biochem., 15:1977:13-9. While this reference discloses that hemoglobin can be detected by peroxide and a pyrazole derivative with phenol, it does not deal with the use of pyrazole derivatives to prevent hemoglobin interference in the presence of peroxide.

In U.S. Pat. No. 4,385,114 there is disclosed the ability of hydroperoxide and a redox indicator to detect the peroxidase activity of hemoglobin. It is this reactivity of hemoglobin with the hydroperoxide which the present invention is designed to inhibit thereby avoiding false positive results in the assay.

Several approaches were explored to prevent hemoglobin interference by the addition of hemoglobin scavengers to the test fluid either by direct addition to the specimen or addition to the reagent with subsequent mixing of the reagent with the specimen. The concentration was from 0.5 to 10 mM. The methods evaluated are summarized in Table 1.

TABLE 1

Compounds Evaluated to Scavenge Hemoglobin

| Scavenger Method | Compounds Evaluated |
| --- | --- |
| Anionic Binding to Fe on Hb | acetoacetate, oxalate, formate, sodium azide |
| Competitive Substrates for Peroxidase | phenindione, oxyphenbutazone, phenbutazone, semicarbazides, 3-methyl-1-phenyl-2-pyrazolin-5-one, antipyrene, 3-methyl-2-pyrazolin-5-one, 5-amino-1-phenyl-4-pyrazolecarboxamide, 4-(3-methyl-5-oxo-2-pyrazolin-1-yl)benzoic acid, 1-(4-nitrophenyl)-3-pyrrolidino-2-pyrazolin-5-one |

TABLE 1-continued

Compounds Evaluated to Scavenge Hemoglobin

| Scavenger Method | Compounds Evaluated |
| --- | --- |
| Fe - binding compounds | captopril, indoxysulfuric acid, imidazole acetic acid, penicillamine, 2-mercaptoethanol |
| Hemoglobin Destroyers | iodate, bromate, periodate. |

Of these methods, anionic binding to iron atoms on the hemoglobin; colorless, competitive substrates for the peroxidase; iron chelators that do not bind to copper and destruction of hemoglobin down to hematin by strong oxidants, only the use of competitive substrates, and of these only a relatively few pyrazoles, were found to be effective to provide hemoglobin resistance without interfering with the creatinine assay. Of those pyrazoles which were tested, the following compounds were found to provide the desired results:

3-methyl-1-phenyl-2-pyrazolin-5-one, 4-(3-methyl-5-oxo-2-pyrazolin-1-yl) benzoic acid, phenbutazone and oxyphenbutazone.

Based on the structures of these compounds, it can be determined that those pyrazoles which are effective to provide the advantages of the present invention must have a phenyl group attached to a nitrogen atom in the pyrazole ring which nitrogen is directly bonded to a carbonyl group. Based on our experiments, the effective pyrazoles should have no exo-cyclic amines, i.e. amines which are not part of the ring but are attached to atoms forming or connected to the ring.

Accordingly, pyrazoles corresponding to the formula:

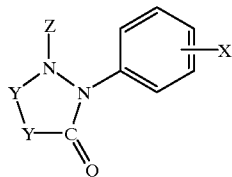

where $X = CO_2H$, H or OH; $Y = CH$, $CH_2$, $C=O$, $CCH_3$ or $CH(CH_2CH_2CH_3)$ and $Z = H$, $C_6H_5$ or none are suitable for use in the present invention.

In the copper$^{+2}$ assay the source of cupric ion may be any soluble copper salt whose anion does not detrimentally interact with the reaction for the colorimetric detection of creatinine. Suitable salts include copper sulfate, nitrate oxide, hydroxide, phosphate, iodide, chloride, bromide, acetate or oxalate. Other soluble cupric salts may be used provided that they allow formation of the CuII•Creatinine complex. Those salts whose anion binds too strongly to the copper will not allow the copperII•Creatinine complex to be formed. Accordingly, CuII complexes such as those formed between cupric ions and EDTA, HEDTA, EGTA and DTPA would not release sufficient CuII for formation of the CuII•Creatinine complex. It has been observed that the citrate and sulfate salts have the lowest blank reactivity and, accordingly, they are preferred. Cupric citrate is particularly preferred due to its exhibiting the least blank reactivity and the greatest formation of the CuII•Creatinine complex. Salts which oxidize the dye in the absence of creatinine are less desirable. Salts such as cupric 2,2'-bipyridine can cause significant oxidation of TMB in the absence of creatinine, and are, therefore, unsuitable for use in the present invention. When copper citrate is used as the cupric ion source, the concentration of citrate ion should be at least that of copper. An excess of citrate ion of at least twice that of the copper ion is preferred to ensure complete complexation of CuII by the citrate.

Typically, when urine is the aqueous fluid being tested, the concentration of cupric ion will be from 5 to 30 mM since the reference range of creatinine in urine is 3 to 20 mM. This range would vary in other fluids such as serum where one would preferably employ a concentration of cupric ion in the range of from 0.05 to 0.30 mM. The Cuprous ion tends to cause some background interference due to oxidation of the dye in the absence of creatinine. Accordingly, CuI salts cannot be used.

Suitable oxidizable indicators include, for example, benzidine; o-tolidine; a 3,3',5,5'-tetraalkylbenzidine wherein the alkyl group includes from one to about six carbon atoms; o-dianisidine; 2,7-diamino-fluorene; bis-(N-ethylquinol-2-one)-azine; (N-methyl--benzthiazol-2-one)-(1-ethyl-3-phenyl-5-methyltriazol-2-one)-azine or combinations thereof.

Suitable hydroperoxides for use in the present invention include cumene hydroperoxide; 5-butyl hydroperoxide; diisopropylbenzene hydroperoxide; 1-hydroxycyclohexane-1-hydroperoxide; 2,5-dimethylhexane-2,5-dihydroperoxide; paramenthane hydroperoxide; 1,4-diisopropylbenzene monohydroperoxide; p-t-butyl-isopropylbenzene hydroperoxide; 2-($\alpha$-hydroperoxyisopropyl)-6-isopropylnaphthalene; tetralin hydroperoxide or combinations thereof.

Typically, the reagent system, comprising the soluble copper salt, hydroperoxide and oxidizable indicator will be dissolved in water. However, organic solvents can be incorporated into the system provided they do not interfere with the assay mechanism. The concentration of the hydroperoxide and oxidizable indicator will normally range from 10 to 150 mM with a range of from 60 to 100 mM being preferred.

In the practice of the invention, the assay can be performed in either the wet or the dry (test strip) format. In carrying out the assay, the test sample is mixed with the copper salt, e.g. cupric citrate, the dye and the hydroperoxide at a buffered pH, preferably from 4.0 to 9.0, through the use of a reagent strip or aqueous and acetonitrile solutions of reagents. Reagent strips are prepared in the conventional manner of dipping an absorbent carrier into an aqueous solution of the cupric salt and buffers, drying the carrier and then dipping it into an organic solution of the dye and hydroperoxide with subsequent drying.

The present invention is further illustrated by the following Examples:

EXAMPLE I

A test strip for the detection of creatinine was prepared by a two dip method in which a strip of Whatman 3 mm filter paper was dipped into a first dip solution, dried at 100° C. for 6–8 minutes and then dipped into a second dip solution followed by drying. The first and second dip solutions were made up as follows:

| Component | Concentration |
|---|---|
| 1st Dip | |
| CuSO$_4$ | 30 mM |
| Citrate | 50 mM |
| Glycerol-2-phosphate as buffer | 750 mM |
| Aerosol IB-45 as surfactant (Pflatz & Baver) | 1.5% (w/v) |

-continued

| Component | Concentration |
|---|---|
| pH | 6.80 |
| Water | |
| 2nd Dip | |
| 3,3',5,5'-Tetramethylbenzidine (TMB) | 33 mM |
| Diisopropyl Benzene Dihydroperoxide (DBDH) | 80 mM |
| Polymer: Plasdone as separator/stabilizer | 3 mM |
| 3-methyl-1-phenyl-2-pyrazolin-5-one | |
| Ethyl orange | 0.032% (w/v) |
| 95% Alcohol | |

This strip was tested for its ability to increase hemoglobin resistance of the formulation by visual and instrumental analysis. A 50 mg/dL creatinine urine standard was spiked with 1 mg/dL hemoglobin. The 50 mg/dL standard with hemoglobin was compared instrumentally using a CLIN-ITEK 50 and CLINITEK 100 reflectance spectrometer and visually using a creatinine color chart versus urine standards containing 50, 100, 200 and 300 mg/dL creatinine. Room temperature stored and stressed (1 week at 60° C.) strips were evaluated. The strip was found to provide a 50 mg/dL result for a urine sample containing 50 mg/dL of creatinine and 10 mg/dL hemoglobin. This is in contrast to the same creatinine reagent, but lacking the pyrazole, which produced a 300 mg/dL result with a urine containing 50 mg/dL of creatinine and 1 mg/dL hemoglobin. The goal of this experiment was twofold. First to provide an assay in which the results obtained using a sample with 50 mg/dL creatinine and 1 mg/dL hemoglobin were the same as those for 50 mg/dL creatinine and no hemoglobin and second to achieve no more than one level increase in reactivity for up to 10 mg/dL hemoglobin (i.e. ≦100 mg/dL creatinine) at the 50 mg/dL creatinine level.

EXAMPLE II

Other pyrazole compounds were screened for their ability to provide resistance to the tendency of hemoglobin to oxidize the TMB indicator in a manner similar to that described in Example I. The pyrazole concentration in the second dip used to prepare the strip was typically 0.5 mM up to 5 mM. The results of these experiments are set out in Table 2.

TABLE 2

Pyrazoles Derivatives Screened in Creatinine Formulation

| Compounds Tested | Result |
|---|---|
| phenbutazone | Hemoglobin resistance |
| oxyphenbutazone | Hemoglobin resistance |
| 3-methyl-1-phenyl-2-pyrazolin-5-one | Hemoglobin resistance |
| 4-(3-methyl-5-oxo-2-prazolin-1-yl)benzoic acid | Hemoglobin resistance |
| antipyrene | Increased hemoglobin activity |
| 1-phenyl-3-pyrazolidione (phenidone) | Decreased hemoglobin and copper creatinine activity |
| 3-methyl-3-pyrazoline-5-one | Increased hemoglobin activity |
| 3-amino-1-phenyl-2-pyrazolin-5-one | Increased hemoglobin activity |
| 5-amino-1-phenyl-4-pyrazole carbaxamide | Increased hemoglobin activity |
| 3-methyl-1-phenylpyrazole | Increased hemoglobin activity |
| indoxyl sulfuric acid | Increased hemoglobin activity |
| imidazole acetic acid | Increased hemoglobin activity |
| 1-(4-nitophenyl)-3-pyrolidnio-2-pyrazolin-5-one | Increased hemoglobin activity |

From the data of Table 2, it can be determined that phenbutazone and oxphenbutazone both demonstrate that two aromatic groups can be attached to two ring nitrogens adjacent to carbonyl groups. The results with 3-methyl-1-phenyl-2-pyrazolin-5-one and 4(3-methyl-5-oxo-2-pyrazoline-1-yl) benzoic acid both show that only one carbonyl and one aromatic group need to be attached to a ring nitrogen to achieve the desired hemoglobin resistance.

The results with antipyrene and phenidone demonstrate that an aromatic group must be attached to the nitrogen next to the carbonyl in order to achieve the desired result, whereas the activity of 5-amino-1-phenyl-4-pyrazole carboxamide and 3-methyl-1-phenyl-pyrazole show that a carboxyl adjacent to the nitrogen is necessary whereas the failure of 3-amino-1-phenyl-2-pyrazoline-5-one shows that an amine substituent is inimical to the reduction of hemoglobin interference. Finally, the results using 1-(4-nitrophenyl)-3-pyrolidino-2-pyrazolin-5-one demonstrate that nitro substitution or the presence of an electron withdrawing group on the aromatic ring renders the pyrazol ineffective for the reduction of hemoglobin interference.

What is claimed is:

1. In an assay for the activity of a metal chelate in a fluid test sample which assay involves combining the metal chelate or precursors thereof with a hydroperoxide and an oxidizable indicator which is oxidizable in the presence of the metal chelate and hydroperoxide to provide a colored response which is indicative of the presence of the metal chelate, the improvement which comprises the inclusion in the assay of a pyrazole derivative which is selected from the group consisting of 3-methyl-1-phenyl-2-pyrazolin-5-one, 4-(3-methyl-5-oxo-2-pyrazolin-1-yl) benzoic acid, phenbutazone and oxyphenbutazone.

2. The assay of claim 1 wherein the metal chelate is a complex of creatinine and cupric ions.

3. The assay of claim 1 wherein the metal chelate is a transition metal porpyhrin.

4. The assay of claim 1 wherein the reagents are in the dry form on an absorbent carrier.

5. The assay of claim 1 wherein the fluid test sample is urine.

6. The assay of claim 1 wherein the concentration of the pyrazole is from 0.5 to 5 mM.

7. The assay of claim 1 where in the pyrazole derivative is 3-methyl-a-phenyl-2-pyrazolin-5-one.

8. An assay for creatinine in urine which comprises combining the urine with cupric ions, a hydroperoxide and an oxidizable dye which provides a colored response in the presence of oxygen free radicals and a hydroperoxide together with a pyrazole derivative which is selected from the group consisting of 3-methyl-1-phenyl-2-pyrazolin-5-one, 4-(3-methyl-5-oxo-2-pyrazolin-1-yl) benzoic acid, phenbutazone and oxyphenbutazone.

9. The assay of claim 8 wherein the concentration of the pyrazole derivative is from 0.5 to 5 mM.

10. The assay of claim 8 wherein the pyrazole derivative is 3-methyl-1-phenyl-2-pyrazolin-5-one.

11. A method for the determination of creatinine in a urine sample which comprises combining the urine sample with $CuSO_4$; citrate; 3,3',5,5'-tetramethylbenzidine and 3-methyl-1-phenyl-2-pyrazolin-5-one to obtain a color change and measuring the magnitude of the color change to determine the concentration of creatine in the urine sample.

* * * * *